United States Patent [19]
Rosen

[11] Patent Number: 6,090,962
[45] Date of Patent: Jul. 18, 2000

[54] PREPARATION OF TITANIUM(II) OR ZIRCONIUM(II) COMPLEXES

[75] Inventor: Robert K. Rosen, Houston, Tex.

[73] Assignee: The Dow Chemical Company, Midland, Mich.

[21] Appl. No.: 09/407,654

[22] Filed: Sep. 28, 1999

Related U.S. Application Data

[60] Provisional application No. 60/106,162, Oct. 29, 1998.

[51] Int. Cl.$^7$ .................................. C07F 17/00; C07F 7/00
[52] U.S. Cl. .................................. 556/11; 556/7; 556/12; 556/20; 556/52; 502/103; 502/117; 526/160; 526/943
[58] Field of Search .................................. 556/7, 11, 12, 556/20, 52; 502/103, 117; 526/160, 943

[56] References Cited

U.S. PATENT DOCUMENTS

| | | | |
|---|---|---|---|
| 5,470,993 | 11/1995 | Devore et al. | 556/11 |
| 5,486,632 | 1/1996 | Devore et al. | 556/11 |
| 5,616,748 | 4/1997 | Newman | 556/11 |

*Primary Examiner*—Porfirio Nazario-Gonzalez

[57] ABSTRACT

Titanium and zirconium complexes comprising one or more, cyclic, delocalized π-bonded ligand groups wherein the metal of said complexes is in the +2 formal oxidation state are prepared in high yield and purity by reaction of the corresponding titanium or zirconium halides in the +3 or +4 oxidation state with a di($C_{1-20}$ alkyl) magnesium reagent. The complexes are used as catalyst components for olefin polymerization catalysts.

7 Claims, No Drawings

PREPARATION OF TITANIUM(II) OR ZIRCONIUM(II) COMPLEXES

CROSS-REFERENCE TO RELATED APPLICATION

This application claims benefit of priority from provisional application 60/106,162, filed Oct. 29, 1998, now abandoned.

BACKGROUND OF THE INVENTION

This invention relates to a process for preparing certain titanium and zirconium complexes comprising one or more cyclic, delocalized ligand groups wherein the metal of said complexes is in the +2 formal oxidation state. In a preferred embodiment, this invention relates to such processes wherein the metal is bonded to the cyclic group or groups via the delocalized π-electrons thereof and also covalently bonded thereto via a divalent ligand group. Such complexes are referred to in the art as "constrained geometry" complexes.

In U.S. Pat. No. 5,512,693, the preparation of the foregoing metal complexes by reaction of the corresponding complex in the +3 or +4 formal oxidation state with an n-alkyl Grignard reagent was disclosed. The technique therein disclosed gives improved yields of the desired product, however, due to limited solubility of the Grignard reagents, generally requires the use of an ether based solvent. Disadvantageously, such solvents need to be scrupulously removed from the resulting product in order not to adversely affect the activity of the resulting metal complex as a catalyst component. This introduces a need for a purification step in the preparation. To further commercial preparation of such complexes, it would be desirable to eliminate the need for such a subsequent purification step.

In U.S. Pat. No. 5,491,246, the above metal complexes were prepared by reaction of the corresponding alkoxide complex in the +3 or +4 formal oxidation state with the diene in the presence of a reducing agent. Suitable reducing agents included metals and compounds, specifically sodium naphthalenide, potassium graphite, lithium alkyls, trihydrocarbyl aluminum compounds and Grignard reagents.

The preparation and characterization of certain biscyclopentadienyl zirconium and hafnium diene complexes are described in the following references: Yasuda, et al., Organometallics, 1, 388 (1982) (Yasuda I); Yasuda, et al., Acc. Chem. Res., 18, 120 (1985), (Yasuda II); Erker et al., Adv. Organomet. Chem., 24, 1 (1985); and U.S. Pat. No. 5,198,401. The preparation of certain Ti, Zr, and Hf monocyclopentadienyl diene complexes lacking the present bridged ligand structure, was described in Yamamoto et al., Organometallics, 8, 105 (1989) (Yamamoto) and Blenkers, J, et al., Organometallics, 6, 459 (1987).

SUMMARY OF THE INVENTION

According to one embodiment of the present invention there is provided a process for preparing a metal complex corresponding to the formula:

(I)

wherein,

M is titanium or zirconium in the +2 formal oxidation state;

Z is an anionic group containing a cyclic group comprising delocalized, π-electrons through which the group is bound to M, said Z group also being bound to Z' through a covalent bond, a dative bond or a divalent bridging group, said Z group having up to 60 atoms other than hydrogen;

Z' is a second Z group or a moiety bound to M via a covalent or dative bond comprising boron, or a member of Group 14 of the Periodic Table of the Elements, and also comprising nitrogen, phosphorus, sulfur or oxygen, said Z' group having up to 60 atoms other than hydrogen;

D is a neutral, conjugated diene, optionally substituted with one or more hydrocarbyl groups, said X having up to 40 carbon atoms;

X' is a neutral Lewis base ligand selected from amines, phosphines and ethers said X' having from 3 to 20 non-hydrogen atoms; and n is a number from 0 to 3;

said process comprising contacting a metal complex according to the formula:

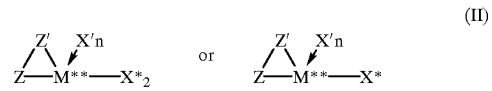

(II)

wherein,

M* is titanium or zirconium in the +3 formal oxidation state;

M** is titanium or zirconium in the +4 formal oxidation state;

X* is halide or $C_{1-20}$ hydrocarblyloxide; and

Z, Z', X' and n are as previously defined;

with a free diene corresponding to D, and subsequently or simultaneously contacting the resulting reaction mixture with a di($C_{1-20}$ alkyl) magnesium compound to form the desired metal complex.

DETAILED DESCRIPTION

The forgoing reduction and diene complex forming process is desirably conducted as one step of a multistep synthesis of the desired diene complexes. According to such a process a complex corresponding to the formula:

wherein,

M is titanium or zirconium in the +2 formal oxidation state;

Z is an anionic group containing a cyclic group comprising delocalized, π-electrons through which the group is bound to M, said Z group also being bound to Z' through a covalent bond, a dative bond or a divalent bridging group, said Z group having up to 60 atoms other than hydrogen;

Z' is a second Z group or a moiety bound to M via a covalent or dative bond comprising boron, or a member of Group 14 of the Periodic Table of the Elements, and also comprising nitrogen, phosphorus, sulfur or oxygen, said Z' group having up to 60 atoms other than hydrogen;

D is a neutral, conjugated diene, optionally substituted with one or more hydrocarbyl groups, said X having up to 40 carbon atoms;

X' is a neutral Lewis base ligand selected from amines, phosphines and ethers said X' having from 3 to 20 non-hydrogen atoms; and n is a number from 0 to 3;

can be prepared by a process comprising:

1) contacting a metal halide compound according to the formula $M^*(X^*)_3X'_n$ or $M^{**}(X^*)_4X'_n$, wherein;

$M^*$ is titanium or zirconium in the +3 formal oxidation state;

$M^{**}$ is titanium or zirconium in the +4 formal oxidation state; and $X^*$ is halide or $C_{1-20}$ hydrocarbyloxide;

with a dianionic salt corresponding to the formula: $M'_2ZZ'$, wherein;

M' is a Group 1 metal, MgCl or MgBr or two M' groups together are a Group 2 metal;

to form an intermediate metal complex according to the formula:

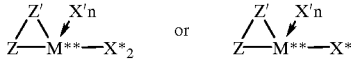

wherein, $M^*$ is titanium or zirconium in the +3 formal oxidation state;

$M^{**}$ is titanium or zirconium in the +4 formal oxidation state;

$X^*$ is halide or $C_{1-20}$ hydrocarblyloxide; and

Z, Z', X' and n are as previously defined; and 2) contacting the intermediate metal complex with a free diene corresponding to D, and subsequently or simultaneously contacting the resulting reaction mixture with a $di(C_{1-20}$ alkyl) magnesium compound to form the desired metal complex.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The diene group, D, does not decompose under reaction conditions used to prepare the complexes of the invention. Under subsequent polymerization conditions, or in the formation of catalytic derivatives of the present complexes, the diene group, D, may undergo chemical reactions or be replaced by another ligand.

The present complexes contain a neutral diene ligand which is coordinated with the metal via delocalized π-electrons thereof, and not through covalent or sigma bonds thereby forming a metallocycle (σ-bound diene) where the metal is in the +4 formal oxidation state. Such a distinction is readily determined by X-ray crystallography or by NMR spectral characterization according to the techniques of Yasuda I, Yasuda II, and Erker, et al., Supra, as well as the references cited therein. By the term "π-complex" is meant both the donation and back acceptance of electron density by the ligand are accomplished using ligand π-orbitals, i. e., the diene is π-bound (π-bound diene).

Preferred transition metal complexes for use herein are dihalide, more preferably dichloride complexes, e.g., complexes of the forgoing formula (II) wherein $X^*$ is halide, more preferably chloride. Preferred $di(C_{1-20})$ hydrocarbyl magnesium compounds are $di(C_{1-20})$ n-alkyl magnesium compounds. More preferably each n-alkyl group has from 1–6 carbon atoms, and most preferably each such group is selected from methyl, ethyl, n-propyl or n-butyl.

The reactions of this invention may be conducted at temperatures from −100° C. to 300° C., preferably from 0 to 80° C. Suitable reaction media for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and styrene, alkyl ethers having from 1 to 4 carbons in each alkyl group; $C_{1-4}$ dialkyl ether derivatives of (poly)alkylene glycols, and tetrahydrofuran. Mixtures of the foregoing are also suitable. As previously mentioned however, the benefits of the process are most noticeable if an aliphatic hydrocarbon solvent is used for the entire process.

All of the steps of the reaction may be performed in sequence in a single reactor vessel without isolation of intermediate products, thereby greatly assisting in the large scale, commercial practice of the process. The recovery procedure usually involves separation of the resulting salt byproducts and residual reducing agent, if any, generally by a simple filtration and, optionally, devolatilization of the reaction medium.

The relative amounts of the respective reagents are not critical to the process. Specifically, the amount of dihydrocarbyl magnesium reagent used is desirably in a molar ratio from 0.25:1 to 3:1 compared to the amount of metal halide or hydrocarbyloxide to be converted, depending on the formal oxidation state of the intermediate metal halide. Preferably, equivalent amounts of reducing agent, based on Mg, are employed for the most economical operation. The amount of diene reagent used is desirably in a molar ratio from 1:1 to 30:1, preferably in a molar ratio from 1:1 to 10:1, compared to the amount of intermediate metal complex.

Preferred neutral Lewis bases include pyridine, diethylether, tetrahydrofuran (THF), 1,2-dimethoxyethane (DME), or tetramethylethylenediamine (TMEDA). Most preferably however, n is zero, that is, there are no neutral Lewis bases present during the preparation.

Preferred metal coordination complexes prepared according to the present invention correspond to the formula:

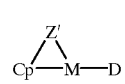

(III)

wherein M and D are as previously defined;

Z' is a moiety bound to M via a covalent bond comprising boron, or a member of Group 14 of the Periodic Table of the Elements, and also comprising nitrogen, phosphorus, sulfur or oxygen, said Z' group having up to 60 atoms other than hydrogen; and Cp is a $C_5H_4$ group covalently bound to Z or such a group substituted with from one to four substituents independently selected from hydrocarbyl, amino, silyl, germyl, halo, cyano, and combinations thereof, said substituent having up to 20 nonhydrogen atoms, and optionally, one or two pairs of such substituents, optionally together with Cp form one or more additional cyclic groups, thereby causing Cp to have a fused ring structure.

More preferred metal coordination complexes prepared according to the present invention correspond to the formula:

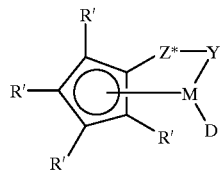

(IV)

wherein:

R' each occurrence is independently selected from hydrogen, amino, hydrocarbyl, silyl, germyl, halo, cyano, and combinations thereof, said R' having up to 20 nonhydrogen atoms, and optionally, one or two pairs of such substituents together each form a $C_{2-10}$ hydrocarbylene group, thereby causing Cp to have a fused ring structure;

D is a neutral, conjugated diene group having up to 30 non-hydrogen atoms, which forms a π-complex with M;

Y is —O—, —S—, —NR*—, —PR*—;

M is titanium or zirconium in the +2 formal oxidation state;

Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$;

wherein:

R* each occurrence is independently hydrogen, or a member selected from hydrocarbyl, silyl, or halohydrocarbyl, said R* having up to 10 non-hydrogen atoms.

Preferably, R' independently each occurrence is hydrogen, hydrocarbyl, silyl, amino, or halohydrocarbyl, said R' having up to 20 non-hydrogen atoms, or one or two pairs of adjacent R' substituents together each form a $C_{2-20}$ hydrocarbylene group, thereby causing Cp to have a fused ring structure. Most preferably, R' is hydrogen, methyl, ethyl, propyl, butyl, pentyl, hexyl, (including where appropriate all isomers), cyclopentyl, cyclohexyl, norbornyl, benzyl, or phenyl or one or two pairs of adjacent R' substituents together cause the entire $C_5R'_4$ group to be an indenyl, tetrahydroindenyl, fluorenyl, tetrahydrofluorenyl, octahydrofluorenyl, s-indacenyl, or cyclopentaphen(l) anthrenyl group. Group 4 metal complexes containing the latter two ligand groups have been disclosed in pending U.S. patent application Ser. No. 08/949,505, filed Oct. 14, 1997 and in provisional application 60/059,000, filed Sep. 15, 1997, the teachings of which are hereby incorporated by reference. They are illustrated by the following structural formulas:

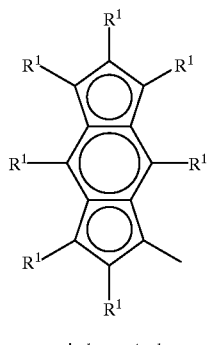

s-indacen-1-yl

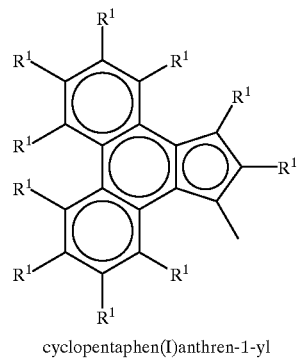

cyclopentaphen(I)anthren-1-yl

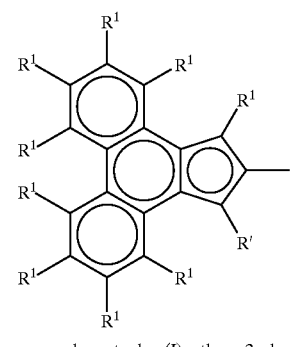

cyclopentaphen(I)anthren-2-yl wherein $R^1$ independently each occurrence is hydrogen, amino, hydrocarbyl, silyl, halo, or halohydrocarbyl, said $R^1$ having up to 20 non-hydrogen atoms Further preferably, at least one of R' or R* is an electron donating moiety. By the term "electron donating" is meant that the moiety is more electron donating than hydrogen. Thus, highly preferably Y is a nitrogen or phosphorus containing group corresponding to the formula —N(R")— or —P(R")—, wherein R" is $C_{1-10}$ hydrocarbyl.

Examples of suitable X groups include: 1,3-pentadiene; 2,4-hexadiene; 1,4-diphenyl-1,3-butadiene; 3-methyl-1,3-pentadiene; 1,4-dibenzyl-1,3-butadiene; 1,4-ditolyl-1,3-butadiene; 1,4-bis(trimethylsilyl)-1,3-butadiene, 1-(4-t-butylphenyl)-4-phenyl-1,3-butadiene, 1-(3-methylphenyl)-4-phenyl-1,3-butadiene, and 1-(3-methoxyphenyl)-4-phenyl-1,3-butadiene.

Most highly preferred metal coordination complexes prepared according to the present invention are amidosilane- or amidoalkanediyl- compounds corresponding to the formula:

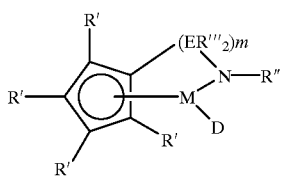

(V)

wherein:

M is titanium;

X is -1,3-pentadiene, 2,4-hexadiene, 1,4-diphenyl-1,3-butadiene, 3-methyl-1,3-pentadiene, 1,4-dibenzyl-1,3-butadiene, 1,4-ditolyl-1,3-butadiene, or 1,4-bis (trimethylsilyl)-1,3-butadiene;

R' is hydrogen, methyl, or phenyl, or one or two pairs of R' groups together cause the ring structure to be an indenyl, tetrahydroindenyl, fluorenyl, octahydrofluorenyl, s-indacenyl, or cyclopenta(l) phenanthrenyl group group;

R" is $C_{1-10}$ hydrocarbyl;

R'" is independently each occurrence hydrogen or $C_{1-10}$ hydrocarbyl;

E is independently each occurrence silicon or carbon; and m is 1 or 2.

Examples of the most highly preferred metal complexes prepared according to the present invention include compounds wherein R" is methyl, ethyl, propyl, butyl, pentyl, hexyl, (including all isomers of the foregoing where applicable), cyclododecyl, norbornyl, benzyl, or phenyl; $(ER'''_2)_m$ is dimethylsilane, or ethanediyl; and the cyclic delocalized π-bonded group is a cyclopentadienyl, tetramethylcyclopentadienyl, indenyl, tetrahydroindenyl, fluorenyl, tetrahydrofluorenyl, 2-methyl-4-phenylindenyl, 2-methyl-4-naphthylindenyl, octahydrofluorenyl, s-indacenyl, or cyclopenta(l)phenanthrenyl group.

Highly preferred diene compounds are: 1,3-pentadiene; 2,4-hexadiene; 1,4-diphenyl-1,3-butadiene; 3-methyl-1,3-pentadiene; 1,4-dibenzyl-1,3-butadiene; 1,4-ditolyl-1,3-butadiene; 1,4-bis(trimethylsilyl)-1,3-butadiene, 1-(4-t-butylphenyl)-4-phenyl-1,3-butadiene, 1-(3-methylphenyl)-4-phenyl-1,3-butadiene, and 1-(3-methoxyphenyl)-4-phenyl-1,3-butadiene. All positional and geometric isomers of the foregoing diene reactants may be utilized.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or diisobutylalumoxane; strong Lewis acids, such as, $C_{1-30}$ hydrocarbyl substituted Group 13 compounds, especially tri(hydrocarbyl)aluminum- or tri(hydrocarbyl)boron compounds and halogenated derivatives thereof, having from 1 to 10 carbons in each hydrocarbyl or halogenated hydrocarbyl group, more especially perfluorinated tri(aryl)boron compounds, and most especially tris (pentafluorophenyl)borane; nonpolymeric, inert, compatible, noncoordinating, ion forming compounds (including the use of such compounds under oxidizing conditions); bulk electrolysis; and combinations of the foregoing activating cocatalysts and techniques. The foregoing activating cocatalysts and activating techniques have been previously taught with respect to different metal complexes in the following references: EP-A-277,003, U.S. Pat. Nos. 5,153,157, 5,064,802, 5,321,106, 5,721,185, 5,350,723 and 5,372,682 the teachings of which are herein incorporated by reference.

The catalysts are suitably employed in the polymerization of olefins according to known Ziegler-Natta polymerization conditions. Especially suited are polymerization temperatures from 0–250° C. and pressures from atmospheric to 1000 atmospheres (0.1 to 100 MPa). Suspension, solution, slurry, gas phase or other process conditions may be employed if desired. A support, especially silica, modified silica (silica modified by calcining, treatment with a trialkylaluminum compound having from 1 to 10 carbons in each alkyl group, or treatment with an alkylalumoxane), alumina, or a polymer (especially polytetrafluoroethylene or a polyolefin) may be employed, and desirably is employed when the catalysts are used in a gas phase or slurry polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}:1$ to $10^{-1}:1$, more preferably from $10^{-12}:1$ to $10^{-5}:1$.

Suitable solvents for solution polymerizations are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), 4-vinylcyclohexene, and vinylcyclohexane. Mixtures of the foregoing are also suitable.

Having described the invention the following examples are provided as further illustration thereof and are not to be construed as limiting. The skilled artisan will appreciate that the invention disclosed herein may be practiced in the absence of any component which has not been specifically disclosed. Unless stated to the contrary all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc.

All solvents were purified using the technique disclosed by Pangborn et al, *Organometallics*, 15, 1518–1520, (1996). All compounds, solutions, and reactions were handled under an inert atmosphere (dry box). $^1H$ and $^{13}C$ NMR shifts were referenced to internal solvent resonances and are reported relative to TMS.

EXAMPLE 1

Preparation of (t-butylamido)(cyclopenta(/)phenanthren-2-yl)dimethylsilanetitanium (II) 1,4-diphenyl-1,3-butadiene

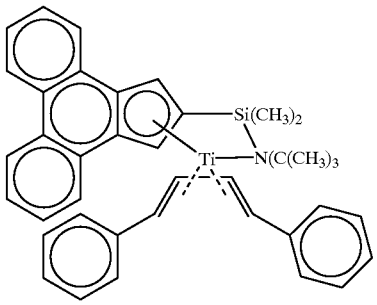

Preparation of lithium 1H-cyclopenta[/]phenanthrene-2-yl

To a 250 ml round bottom flask containing 1.42 g (0.00657 mole) of 1H-cyclopenta[/]phenanthrene and 120 ml of benzene was added dropwise, 4.2 ml of a 1.60 M solution of n-BuLi in mixed hexanes. The solution was allowed to stir overnight. The lithium salt was isolated by filtration, washing twice with 25 ml benzene and drying under vacuum. Isolated yield was 1.426 g (97.7 percent). $^1$H NMR analysis indicated the predominant isomer was substituted at the 2 position.

Preparation of (1H-cyclopenta[/]phenanthrene-2-yl)dimethylchlorosilane

To a 500 ml round bottom flask containing 4.16 g (0.0322 mole) of dimethyidichlorosilane (Me2SiCl2) and 250 ml of tetrahydrofuran (THF) was added dropwise a solution of 1.45 g (0.0064 mole) of lithium 1H-cyclopenta[/]phenanthrene-2-yl in THF. The solution was stirred for approximately 16 hours, after which the solvent was removed under reduced pressure, leaving an oily solid which was extracted with toluene, filtered through diatomaceous earth filter aid, washed twice with toluene and dried under reduced pressure. Isolated yield was 1.98 g (99.5 percent).

Preparation of (1H-cyclopenta[/]phenanthrene-2-yl)dimethyl(t-butylamino)silane

To a 500 ml round bottom flask containing 1.98 g (0.0064 mole) of (1H-cyclopenta[/]phenanthrene-2-yl)dimethylchlorosilane and 250 ml of hexane was added 2.00 ml (0.0160 mole) of t-butylamine. The reaction mixture was allowed to stir for several days, then filtered using diatomaceous earth filter aid, washed twice with hexane. The product was isolated by removing residual solvent under reduced pressure. The isolated yield was 1.98 g (88.9 percent).

Preparation of dilithio (1H-cyclopenta[/]phenanthrene-2-yl)dimethyl(t-butylamido)silane To a 250 ml round bottom flask containing 1.03 g (0.0030 mole) of (1H-cyclopenta[/]phenanthrene-2-yl)dimethyl(t-butylamino)silane) and 120 ml of benzene was added dropwise 3.90 ml of a solution of 1.6 M n-BuLi in mixed hexanes. The reaction mixture was stirred for approximately 16 hours. The product was isolated by filtration, washed twice with benzene and dried under reduced pressure. Isolated yield was 1.08 g (100 percent).

Preparation of (1H-cyclopenta[/]phenanthrene-2-yl)dimethyl(t-butylamido)silanetitanium dichloride To a 250 ml round bottom flask containing 1.17 g (0.0030 mole) of TiCl$_3$.3THF and about 120 ml of THF was added at a fast drip rate about 50 ml of a THF solution of 1.08 g of dilithio (1H-cyclopenta[/]phenanthrene-2-yl)dimethyl(t-butylamido)silane. The mixture was stirred at about 20° C. for 1.5 h at which time 0.55 gm (0.002 mole) of solid PbCl$_2$ was added. After stirring for an additional 1.5 h the THF was removed under vacuum and the reside was extracted with toluene, filtered and dried under reduced pressure to give an orange solid. Yield was 1.31 g (93.5 percent).

Preparation of (1H-cyclopenta[/]phenanthrene-2-yl)dimethyl(t-butylamido)silanetitanium dichloride In an inert atmosphere glove box, 5.00 g (10.8 mmol) of (t-butylamido)(cyclopenta[/]phenanthren-2-yl)dimethylsilanetitanium dichloride and 2.23 g (10.8 mmol) of 1,4-diphenyl-1,3-butadiene were slurried in 100 mL of toluene. While stirring, 12.15 mL of a 0.98 M toluene solution of (ethyl)(n-butyl)Mg in toluene (12 mmol) was added and the mixture was heated to the reflux temperature and maintained at that temperature for 3 h. The mixture's color changed to a dark red-purple color. The reaction mixture was cooled to room temperature (20° C.) and the volatile materials removed under reduced pressure. The reaction mixture was filtered through a 10–15 µm fritted funnel using diatomaceous earth filter aid giving the desired product as a 2.1 weight percent solution. Yield was 77 percent.

EXAMPLE 2

(t-butylamido)dimethyl(tetramethylcyclopentadienyl)silanetitanium (II) 1,4-diphenyl-1,3-butadiene (t-Butylamido)dimethyl(tetramethylcyclopentadienyl)silanetitanium dichloride, (1.00 g, 2.4 mmol) was dissolved in 20 mL of toluene. Trans,trans-1,4-diphenyl-1,3-butadiene (0.56 g, 2.7 mmol) was added using an additional 10 mL of toluene. While stirring, butylethylmagnesium (Akzo Nobel, 2.2 mL of a 1.36 M solution) was added, resulting in an immediate darkening of the solution color. The mixture was stirred for four days at ambient temperature. At the end of this time, the mixture was filtered using a 0.45 µm syringe filter (25 mm diameter) and a glass fiber pre-filter. The toluene was removed under reduced pressure, and the solid was triturated (2×10 mL) with pentane. A purple solid was obtained; yield 1.12 g (82 percent).

EXAMPLE 3

Preparation of (t-butylamido)dimethyl(4-pyrrolidinoinden-1-yl)silanetitanium (II) 1,3-pentadiene

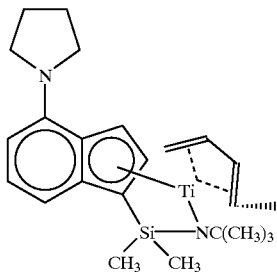

(t-Butylamido)dimethyl(4-pyrrolidinoinden-1-yl)silanetitanium dichloride (307 g, 0.715 mol), hexane (3.0 L), piperylene (182 g), and 1.07 mol of 1,3-pentadiene, (additionally containing 110 g of inert, hydrocarbon components), were added to a 5 L glass reactor with resin kettle lid equipped with a stirrer assembly (a glass stirrer shaft with teflon paddle and stirrer seal), and a pair of ground glass stoppers. A solution of butylethylmagnesium in heptane (564 g, 0.715 mol BuEtMg) was loaded into a side arm vented addition funnel, stoppered with a ground glass stopper, and attached to the reactor through a port opened by removal of one of the ground glass stoppers. The BuEtMg solution was added dropwise over 1 hour, at room temperature, while the dichloride solution was stirred and cooled with a fan. A precipitate was noticed after 100 grams of BuEtMg had been added. The additional funnel was replaced with a condenser, then the slurry was heated at reflux for 4 hours, followed by cooling (90 minutes) to 25° C. The slurry was then vacuum filtered through a bed of diatomaceous earth filter aid packed on a fine fritted glass funnel. During the filtration a tacky, black, tar-like product which collected on the filter was removed with a spatula and shaken with hexane (400 mL.) to extract additional product. This slurry was also filtered using diatomaceous earth filter aid and the combined filtrates were added to a clean, predried, 5 L glass reactor with resin kettle type lid equipped with a Schlenk adaptor, stirrer assembly (a glass stirrer shaft with teflon paddle and stirrer seal), and ground glass stopper. The solvent was removed under dynamic vacuum, the stirrer was turned off, and the reactor contents were maintained under vacuum (1 Torr/16 hours) to remove the last traces of hexane. The product (276 g, 0.645 mol) was recovered in 90 percent isolated yield as a tacky, brown solid.

EXAMPLE 4

Preparation of (t-butylamido)dimethyl(2-methyl-s-indacen-1-yl)silanetitanium (II) (1,3-pentadiene)

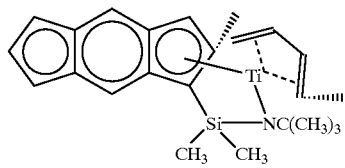

(t-Butylamido)dimethyl(tetramethylcyclopentadienyl) silanetitanium (0.50 g, 1.2 mmol) was slurried in 30 mL of cyclohexane in a 100 mL flask. Piperylene (0.359 mL, 3.6 mmol) and BEM (1.423 mL, 1.32 mmol) were added. The reaction was heated to reflux for 90 minutes. After cooling, the reaction was filtered through diatomaceous earth filter aid on a medium porosity glass fritted funnel. The solvent was removed under reduced pressure to afford the desired product 0.418 g (84 percent) as a dark solid.

What is claimed is:

1. A process for preparing a metal complex corresponding to the formula:

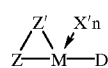

(I)

wherein,
M is titanium or zirconium in the +2 formal oxidation state;
Z is an anionic group containing a cyclic group comprising delocalized, π-electrons through which the group is bound to M, said Z group also being bound to Z' through a covalent bond, a dative bond or a divalent bridging group, said Z group having up to 60 atoms other than hydrogen;

Z' is a second Z group or a moiety bound to M via a covalent or dative bond comprising boron, or a member of Group 14 of the Periodic Table of the Elements, and also comprising nitrogen, phosphorus, sulfur or oxygen, said Z' group having up to 60 atoms other than hydrogen;

D is a neutral, conjugated diene, optionally substituted with one or more hydrocarbyl groups, said X having up to 40 carbon atoms;

X' is a neutral Lewis base ligand selected from amines, phosphines and ethers said X' having from 3 to 20 non-hydrogen atoms; and n is a number from 0 to 3;

said process comprising contacting a metal complex according to the formula:

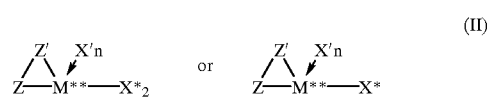

(II)

wherein,
M* is titanium or zirconium in the +3 formal oxidation state;
M** is titanium or zirconium in the +4 formal oxidation state;
X* is halide or $C_{1-20}$ hydrocarblyloxide; and
Z, Z', X' and n are as previously defined;
with a free diene corresponding to D, and subsequently or simultaneously contacting the resulting reaction mixture with a di($C_{1-20}$ alkyl) magnesium compound to form the desired metal complex.

2. A process according to claim 1 wherein the free diene corresponding to D is 1,4-diphenyl-1,3-butadiene; 1,3-pentadiene; 1,4-dibenzyl-1,3-butadiene; 2,4-hexadiene; 3-methyl-1,3-pentadiene; 1,4-ditolyl-1,3-butadiene; or 1,4-bis(trimethylsilyl)-1,3-butadiene.

3. A process according to claim 1 wherein the resulting metal complex corresponds to the formula:

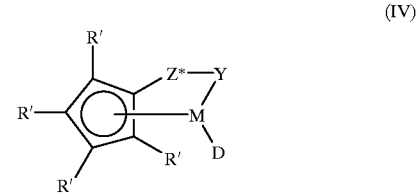

(IV)

wherein:
R' each occurrence is independently selected from hydrogen, amino, hydrocarbyl, silyl, germyl, halo, cyano, and combinations thereof, said R' having up to 20 nonhydrogen atoms, and optionally, one or two pairs of such substituents together each form a $C_{2-10}$ hydrocarbylene group, thereby causing Cp to have a fused ring structure;

D is a neutral, conjugated diene group having up to 30 non-hydrogen atoms, which forms a π-complex with M;

Y is —O—, —S—, —NR*—, —PR*—;

M is titanium or zirconium in the +2 formal oxidation state;

Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$;

wherein:

R* each occurrence is independently hydrogen, or a member selected from hydrocarbyl, silyl, or halohydrocarbyl, said R* having up to 10 non-hydrogen atoms.

4. A process according to claim 3 wherein R' independently each occurrence is hydrogen, hydrocarbyl, silyl, amino, or halohydrocarbyl, said R' having up to 20 non-hydrogen atoms, or one or two pairs of adjacent R' substituents together each form a $C_{2-20}$ hydrocarbylene group, thereby causing Cp to have a fused ring structure.

5. A process according to claim 4 wherein R' is hydrogen, methyl, ethyl, propyl, butyl, pentyl, hexyl, (including where appropriate all isomers), cyclopentyl, cyclohexyl, norbornyl, benzyl, or phenyl or one or two pairs of adjacent R' substituents together cause the entire $C_5R'_4$ group to be an indenyl, tetrahydroindenyl, fluorenyl, tetrahydrofluorenyl, octahydrofluorenyl, s-indacenyl, or cyclopentaphen(/) anthrenyl group.

6. A process according to claim 5 wherein Y is a nitrogen or phosphorus containing group corresponding to the formula —N(R")— or —P(R")—, wherein R" is $C_{1-10}$ hydrocarbyl.

7. A process according to claim 1 wherein each hydrocarbyl group of the di($C_{1-20}$ hydrocarbyl) magnesium compound is n-alkyl.

* * * * *